United States Patent
Behrooz et al.

(10) Patent No.: US 12,259,944 B1
(45) Date of Patent: Mar. 25, 2025

(54) SYSTEMS AND METHODS FOR SIMULATING MEDICAL IMAGES USING GENERATIVE ADVERSARIAL NETWORKS

(71) Applicant: Verily Life Sciences LLC, South San Francisco, CA (US)

(72) Inventors: Ali Behrooz, San Bruno, CA (US); Cheng-Hsun Wu, San Bruno, CA (US)

(73) Assignee: VERILY LIFE SCIENCES LLC, Dallas, TX (US)

( * ) Notice: Subject to any disclaimer, the term of this patent is extended or adjusted under 35 U.S.C. 154(b) by 408 days.

(21) Appl. No.: 17/447,235

(22) Filed: Sep. 9, 2021

Related U.S. Application Data

(60) Provisional application No. 62/706,768, filed on Sep. 9, 2020.

(51) Int. Cl.
| | |
|---|---|
| *G06F 18/214* | (2023.01) |
| *G06F 3/0482* | (2013.01) |
| *G06F 3/04847* | (2022.01) |
| *G06N 3/045* | (2023.01) |

(52) U.S. Cl.
CPC .......... *G06F 18/214* (2023.01); *G06F 3/0482* (2013.01); *G06F 3/04847* (2013.01); *G06N 3/045* (2023.01)

(58) Field of Classification Search
CPC .. G06F 18/214; G06F 3/0482; G06F 3/04847; G06N 3/045
See application file for complete search history.

(56) References Cited

U.S. PATENT DOCUMENTS

| | | | |
|---|---|---|---|
| 10,264,971 B1* | 4/2019 | Kennedy | A61B 5/6804 |
| 11,580,673 B1* | 2/2023 | Ren | G06N 3/0464 |
| 2019/0018933 A1 | 1/2019 | Oono et al. | |
| 2019/0110754 A1* | 4/2019 | Rao | G06N 7/00 |
| 2019/0188446 A1* | 6/2019 | Wu | G06V 20/695 |
| 2019/0259492 A1 | 8/2019 | Reicher et al. | |

(Continued)

OTHER PUBLICATIONS

Quiros, Adalberto Claudio, Roderick Murray-Smith, and Ke Yuan. "PathologyGAN: Learning deep representations of cancer tissue." arXiv preprint arXiv: 1907.02644 (2019). (Year: 2019).*

(Continued)

*Primary Examiner* — Utpal D Shah
(74) *Attorney, Agent, or Firm* — Kilpatrick Townsend & Stockton LLP

(57) ABSTRACT

One disclosed example method for simulated medical images using GANs includes receiving, by a generative adversarial network ("GAN"), a plurality of training images, the training images associated with an affliction and depicting different stages of progression for the affliction; generating, using the GAN, a latent space based on the training images, the latent space comprising a first set of data points indicating parameters associated with the training images; generating, using the GAN, a second set of data points in the latent space based on simulated images generated from the latent space, the simulated images based at least in part on the first set of data points; after generating the second set of data points: receiving a request for a first simulated image associated with the affliction; and generating and outputting, by the GAN, the first simulated image based on the latent space.

27 Claims, 9 Drawing Sheets

(56) References Cited

U.S. PATENT DOCUMENTS

| | | | |
|---|---|---|---|
| 2021/0118136 A1* | 4/2021 | Hassan-Shafique | G16B 20/20 |
| 2021/0158503 A1* | 5/2021 | Li | G06F 18/214 |
| 2021/0345934 A1* | 11/2021 | Landgraf | A61B 5/6898 |
| 2021/0374599 A1* | 12/2021 | Kozloski | G06N 20/00 |
| 2022/0067982 A1* | 3/2022 | Pardeshi | G06N 3/047 |
| 2022/0068037 A1* | 3/2022 | Pardeshi | G06T 7/70 |
| 2022/0084204 A1* | 3/2022 | Li | G06N 3/08 |
| 2022/0165413 A1* | 5/2022 | Murphy | G16H 50/70 |
| 2023/0177682 A1* | 6/2023 | Xiao | G06T 7/11 382/133 |
| 2024/0144477 A1* | 5/2024 | Kanan | G16H 30/40 |

OTHER PUBLICATIONS

Belthangady et al., "Applications, promises, and pitfalls of deep learning for fluorescence image reconstruction", Nature methods 16.12 (2019): 1215-1225.

Goodfellow et al., "Generative Adversarial Nets", Advances in Neural Information Processing Systems 27 (NIPS 2014), Jun. 2014, 9 pages.

Heljakka et al., "Towards Photographic Image Manipulation with Balanced Growing of Generative Autoencoders", arXiv preprint arXiv:1904.06145 (2019), 23 pages.

Jin et al., "CT-realistic lung nodule simulation from 3D conditional generative adversarial networks for robust lung segmentation", International Conference on Medical Image Computing and Computer-Assisted Intervention. Springer, Cham, 2018.

Karras et al., "A style-based generator architecture for generative adversarial networks", arXiv preprint arXiv:1812.04948 (2018), 12 pages.

Wang et al., "High-resolution image synthesis and semantic manipulation with conditional gans", Proceedings of the IEEE conference on computer vision and pattern recognition, 2018, 10 pages.

Yi et al., "Generative Adversarial Networkin Medical Imaging: A Review", arXiv preprint arXiv:1809.07294 (2018).

Zhang et al., "Cascaded generative and discriminative learning for microcalcification detection in breast mammograms", Proceedings of the IEEE/CVF Conference on Computer Vision and Pattern Recognition (2019), 9 pages.

* cited by examiner

SYSTEMS AND METHODS FOR SIMULATING MEDICAL IMAGES USING GENERATIVE ADVERSARIAL NETWORKS

CROSS-REFERENCE TO RELATED APPLICATIONS

The present application claims the benefit of U.S. Provisional Patent Application 62/706,768, filed Sep. 9, 2020, titled "Systems And Methods For Simulating Medical Images Using Generative Adversarial Networks", the entirety of which is hereby incorporated by reference.

FIELD

The present application generally relates to adversarial networks and more particularly relates to systems and methods for simulating medical images using generative adversarial networks.

BACKGROUND

After a patient has tissue biopsied for examination, a pathologist will examine a portion of the tissue, such as a slice of the tissue. In examining the tissue, the pathologist may stain the tissue and capture an image of the stained tissue using magnification optics. The captured image may then be displayed on a screen for the pathologist to examine to identify potential disease or other medical conditions.

SUMMARY

Various examples are described for systems and methods for simulating medical images using generative adversarial networks. One example method for simulated medical images using GANs includes receiving, by a generative adversarial network ("GAN"), a plurality of training images, the training images associated with an affliction and depicting different stages of progression for the affliction; generating, using the GAN, a latent space based on the training images, the latent space comprising a first set of data points indicating parameters associated with the training images; generating, using the GAN, a second set of data points in the latent space based on simulated images generated from the latent space, the simulated images based at least in part on the first set of data points; after generating the second set of data points: receiving a request for a first simulated image associated with the affliction; and generating and outputting, by the GAN, the first simulated image based on the latent space.

Another example method includes receiving, by a generative adversarial network ("GAN"), a plurality of training images, the training images associated with an affliction and depicting different stages of progression for the affliction; generating, using the GAN, a latent space based on the training images, the latent space comprising a first set of data points indicating parameters associated with the training images; and generating, using the GAN, a second set of data points in the latent space based on simulated images generated from the latent space, the simulated images based at least in part on the first set of data points.

A further example method includes receiving, by a generative adversarial network ("GAN"), a seed image associated with an affliction; and generating and outputting, using the GAN, a severity score based on a latent space and the seed image, the latent space comprising: a first set of data points indicating parameters associated with a set of training images associated with the affliction and depicting different stages of progression for the affliction, and a second set of data points generated by the GAN based on the first set of data points, the parameters comprising indications of severity level of the affliction.

One example device includes a non-transitory computer-readable medium; and a processor in communication with the non-transitory computer-readable medium, the processor configured to execute processor-executable instructions stored in the non-transitory computer-readable medium to receive, by a generative adversarial network ("GAN"), a plurality of training images, the training images associated with an affliction and depicting different stages of progression for the affliction; generate, using the GAN, a latent space based on the training images, the latent space comprising a first set of data points indicating parameters associated with the training images; generate, using the GAN, a second set of data points in the latent space based on simulated images generated from the latent space, the simulated images based at least in part on the first set of data points; after generating the second set of data points: receive a request for a first simulated image associated with the affliction; and generate and output by the GAN, the first simulated image based on the latent space.

Another example device includes a non-transitory computer-readable medium; and a processor in communication with the non-transitory computer-readable medium, the processor configured to execute processor-executable instructions stored in the non-transitory computer-readable medium to receive, by a generative adversarial network ("GAN"), a plurality of training images, the training images associated with an affliction and depicting different stages of progression for the affliction; generate, using the GAN, a latent space based on the training images, the latent space comprising a first set of data points indicating parameters associated with the training images; and generate, using the GAN, a second set of data points in the latent space based on simulated images generated from the latent space, the simulated images based at least in part on the first set of data points.

A further device includes a non-transitory computer-readable medium; and a processor in communication with the non-transitory computer-readable medium, the processor configured to execute processor-executable instructions stored in the non-transitory computer-readable medium to receive, by a generative adversarial network ("GAN"), a seed image associated with an affliction; and generate and output, using the GAN, a severity score based on a latent space and the seed image, the latent space comprising: a first set of data points indicating parameters associated with a set of training images associated with the affliction and depicting different stages of progression for the affliction, and a second set of data points generated by the GAN based on the first set of data points, the parameters comprising indications of severity level of the affliction.

One example non-transitory computer-readable medium includes processor-executable instructions configured to cause a processor to receive, by a generative adversarial network ("GAN"), a plurality of training images, the training images associated with an affliction and depicting different stages of progression for the affliction; generate, using the GAN, a latent space based on the training images, the latent space comprising a first set of data points indicating parameters associated with the training images; generate, using the GAN, a second set of data points in the latent space based on simulated images generated from the latent space, the simulated images based at least in part on the first set of data points; after generating the second set of data points: receive a request for a first simulated image associated with the affliction; and generate and output by the GAN, the first simulated image based on the latent space.

Another example non-transitory computer-readable medium includes processor-executable instructions configured to cause a processor to receive, by a generative adversarial network ("GAN"), a plurality of training images, the training images associated with an affliction and depicting different stages of progression for the affliction; generate, using the GAN, a latent space based on the training images, the latent space comprising a first set of data points indicating parameters associated with the training images; and generate, using the GAN, a second set of data points in the latent space based on simulated images generated from the latent space, the simulated images based at least in part on the first set of data points.

A further example non-transitory computer-readable medium includes processor-executable instructions configured to cause a processor to receive, by a generative adversarial network ("GAN"), a seed image associated with an affliction; and generate and output, using the GAN, a severity score based on a latent space and the seed image, the latent space comprising: a first set of data points indicating parameters associated with a set of training images associated with the affliction and depicting different stages of progression for the affliction, and a second set of data points generated by the GAN based on the first set of data points, the parameters comprising indications of severity level of the affliction.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
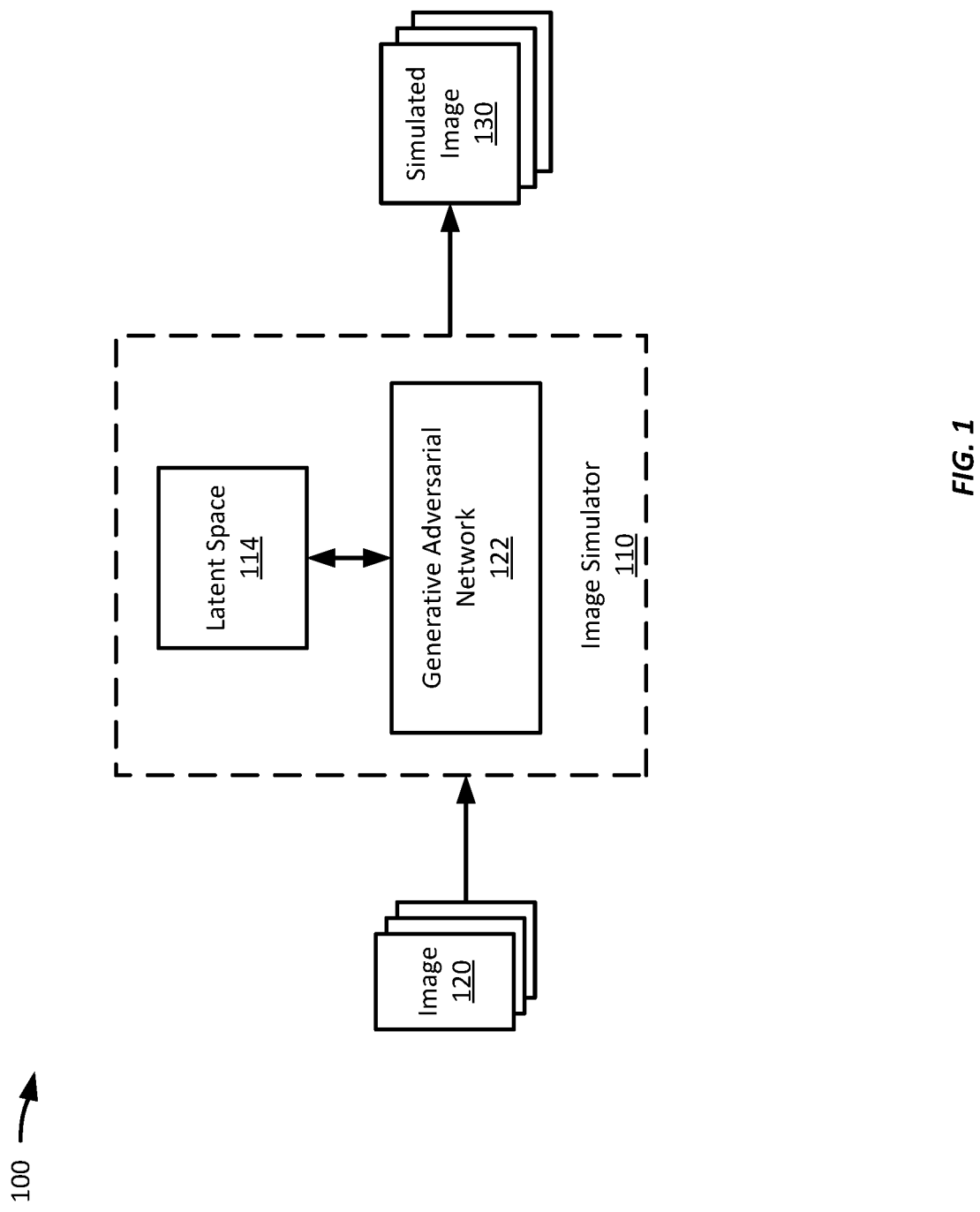
FIG. 1 shows an example system for simulating medical images using generative adversarial networks.

Examples are described herein in the context of systems and methods for simulating medical images using generative adversarial networks. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Images of tissue samples biopsied from a patient may be examined by a pathologist to detect a disease or medical condition (collectively an "affliction") or to monitor the progression of that affliction. Recognizing signs of different afflictions in medical images is a difficult task and requires extensive training of medical personnel, including medical doctors. One way to provide training is to provide medical images to personnel during training and teach them various indicators of different afflictions. Over time, they will learn to recognize different afflictions from medical images, as well as the level of progression or severity of the affliction. Once they are sufficiently trained, they may then begin to examine tissue samples or medical images to diagnose or monitor different afflictions.

However, various difficulties present themselves when training medical personnel. First, sufficient numbers of example medical images are needed to enable medical professionals to recognize signs or hallmarks of an affliction. These example images must show not only different afflictions, but also different stages or severities of those afflictions. In addition, once a piece of tissue has been resected for pathological analysis, that tissue has been removed from the patient and thus it is not possible to see how that tissue sample would have changed over time as the affliction progressed. Thus, a tissue sample is a single snapshot in time of the state of the tissue when sampled and future samples will necessarily be of a different part of the tissue.

To help provide additional opportunities for training or to project affliction progression for a patient, systems and methods according to this disclosure enable simulating or synthesizing longitudinal medical images using generative adversarial networks. Generative adversarial networks (each a "GAN") are a class of machine learning techniques that use a generator and a discriminator to develop a multidimensional data space, referred to as a "latent space" herein, from which information may be extracted to generate a desired result. The process of developing the latent space is called "training" and involves using the generator and some seed data to generate proposed outputs, e.g., reconstructions of the seed data or wholly new outputs based on interpolations of the data in the latent space. The discriminator receives the proposed output data and, using a predetermined statistical distribution, e.g., normal distribution, uniform distribution, etc., determines whether the proposed output sufficiently conforms to the statistical distribution to be identified as a member of the latent space. If the output is statistically acceptable, it will be accepted and the latent space will be updated with the output data. If the output is not statistically acceptable, it will be rejected and the latent space will be adjusted to avoid generating similar output data in the future.

To generate a simulated image, a suitable GAN, such as an autoencoder GAN ("AEGAN"), is trained using a set of training images of tissue samples for a particular affliction and at various stages of the corresponding affliction. The training images are supplied to the encoder, which encodes them into the latent space and the AEGAN then develops the latent space as discussed above. In some examples, the images may be accompanied by additional information, e.g., labels, that identifies the type of affliction, the severity of the affliction, the age of the patient, the patient's gender, etc.

Once the AEGAN is sufficiently trained, a user may access the AEGAN and request a simulated image be generated for the affliction having a desired state of progression or severity. For example, if the AEGAN is trained on medical images of melanoma, a user may request an image showing a stage 3 melanoma. Alternatively, the user may supply a pathology image for melanoma at a particular stage of development and request a generated image at a different stage, e.g., at a more advanced stage. The AEGAN then generates an image based on the request and the trained latent space, and outputs the image for the user to view. It is also possible to supply an image to the AEGAN without an assigned stage, and the AEGAN can determine the stage based on the input image's determined position within the AEGAN's latent space.

Using such a system, a user may view large numbers of different simulated medical images without needing access to a large library of real images, and thus may be trained more efficiently and inexpensively. Such images may be expensive or otherwise difficult to obtain in large numbers. In addition, once an image has been reviewed, it may not be as effective for training the same individual if re-used a second or third time. Thus, a system that can generate realistic but simulated medical images may provide substantial benefits to medical personnel.

This illustrative example is given to introduce the reader to the general subject matter discussed herein and the disclosure is not limited to this example. The following sections describe various additional non-limiting examples and examples of systems and methods for simulating medical images using generative adversarial networks.

Referring now to FIG. 1, FIG. 1 illustrates an example system 100 for simulating medical images using GANs. In this example, the system includes an image simulator 110, which includes a GAN 122 that interacts with a latent space 114. The image simulator 110 can accept images 120 and also generate and output simulated images 130. In this example the GAN 122 is an AEGAN, but in other examples any suitable GAN may be used. Further different types of autoencoders may be employed by the AEGAN in different examples, such as variational autoencoders, e.g., in a VAE-GAN.

In this example, the system 100 trains the GAN 122 during a training phase to develop the latent space 114. During training, training images, e.g., images 120, are provided to the GAN 122, which parameterizes each image and inserts it into the latent space 114. Training images may be of any suitable type of medical image, such as pathology images, fluoroscopy images, ultrasound images, CT images, MRI images, etc. As data from successive images is parameterized and added to the latent space, it increases the density of information stored in the latent space 114. However, absent a significant number of training images, e.g., tens or hundreds of thousands of training images, the latent space 114 will lack sufficient density to generate realistic simulated images. Thus, the GAN 122 will further improve the density of the latent space 114 by generating simulated images and, using a discriminator, determine whether the generated images are sufficiently realistic to be added to the latent space 114. As images are generated, the discriminator determines whether they are "realistic," i.e., it determines the image is a simulated image rather than an real image, based on a predetermined expected data distribution within the latent space. If the discriminator correctly identifies a simulated image, the generator's model is updated to better interpolate the data within the latent space. If the discriminator incorrectly identifies a simulated image as a real image, the discriminator's model is updated to better apply the distribution function to the data in the latent space.

In this example, the GAN 122 is trained using both training images as well as corresponding severity scores (or corresponding stages of development of an affliction). Thus, each image supplied to the image simulator 110 will have a corresponding severity score. Consequently, data in the latent space 114 will also have corresponding severity scores. Such information may be used both by the generator and the discriminator as part of the training exercise discussed above, as well as when generating simulated images after then GAN 122 has been trained.

Once the latent space 114 has been sufficiently densely populated, the image simulator may then generate simulated images. In this example, a user may request a simulated image and provide a desired severity score. The image simulator 110 will then generate a simulated image based on the latent space 114 and the supplied severity score, in the same way that it generated simulated images during the training phase. The simulated image is then output, such as by displaying it on a screen or saving it as an image file to a storage device.

Figure 2:
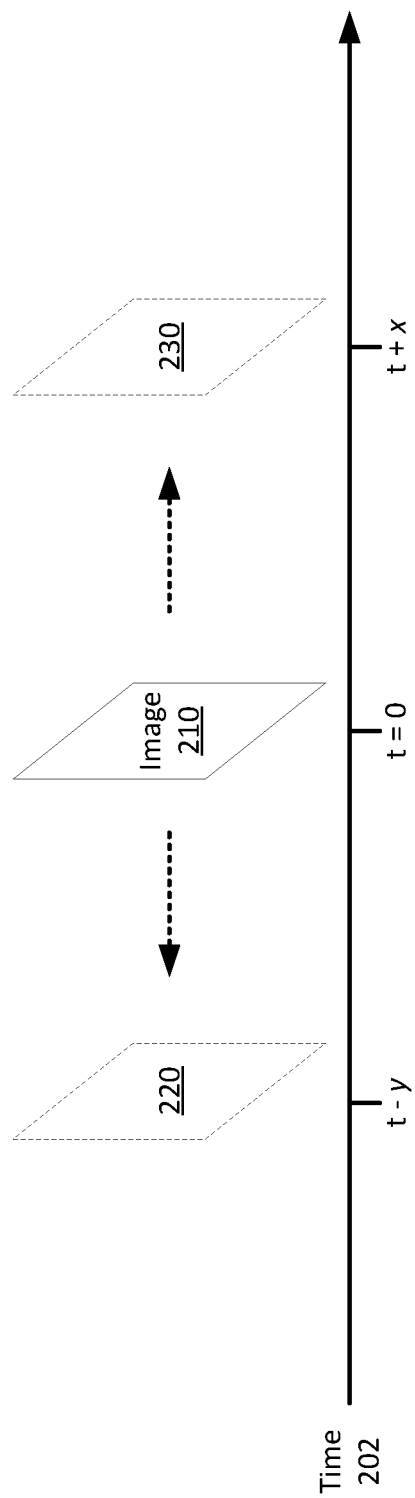
FIG. 2 shows an example illustration of a timeline of images showing progression of a disease or medical condition.

In addition to supplying a severity score, in some examples, the user may also provide an image (called a "seed image") on which to base a simulated image. As discussed above, a pathology sample represents a snapshot of the tissue in time, but it is not possible to see how the sample will change over time, since it has been resected and will not continue to grow. This is illustrated in FIG. 2, which shows a seed image 210 on a timeline 202. Depending on a particular user's interests, it may be desirable to show progression of the affliction shown in the seed image at a different point in time, such as simulated image 220, at a time (t−y) or stage preceding the biopsy, or simulated 230 at some later time (t+x) or stage of development.

For example, the user may obtain a pathology image from a patient and supply it as a seed image to the image simulator 110 along with a severity score. The user may then request a simulated image and supply a different severity score. The image simulator may then parameterize the seed image as it would during a training phase and then adjust those parameters based on the difference between the severity score associated with the seed image and the severity score for the requested image. Because the image simulator 110 has been trained, the adjustments to the parameters extracted from the seed image and based on the latent space will result in a realistic simulated image. Further, in some examples, the seed image may be incorporated into the latent space or used to further train the image simulator 110.

A further extension of such an image simulator 110 may enable a user to provide a seed image and a severity score and then request various simulated images with different severity scores, such as by sliding a slider and seeing the seed image apparently change as the slider moves. Such a technique may allow the user to view something akin to an animation of the progression of the affliction based on the seed image. This could be used for training or other educational purposes for medical professionals, or to illustrate to a patient how the affliction will progress if they do not undergo treatment. Using such a system, a user may quickly and efficiently generate simulated images of afflictions of interest.

Figure 3:
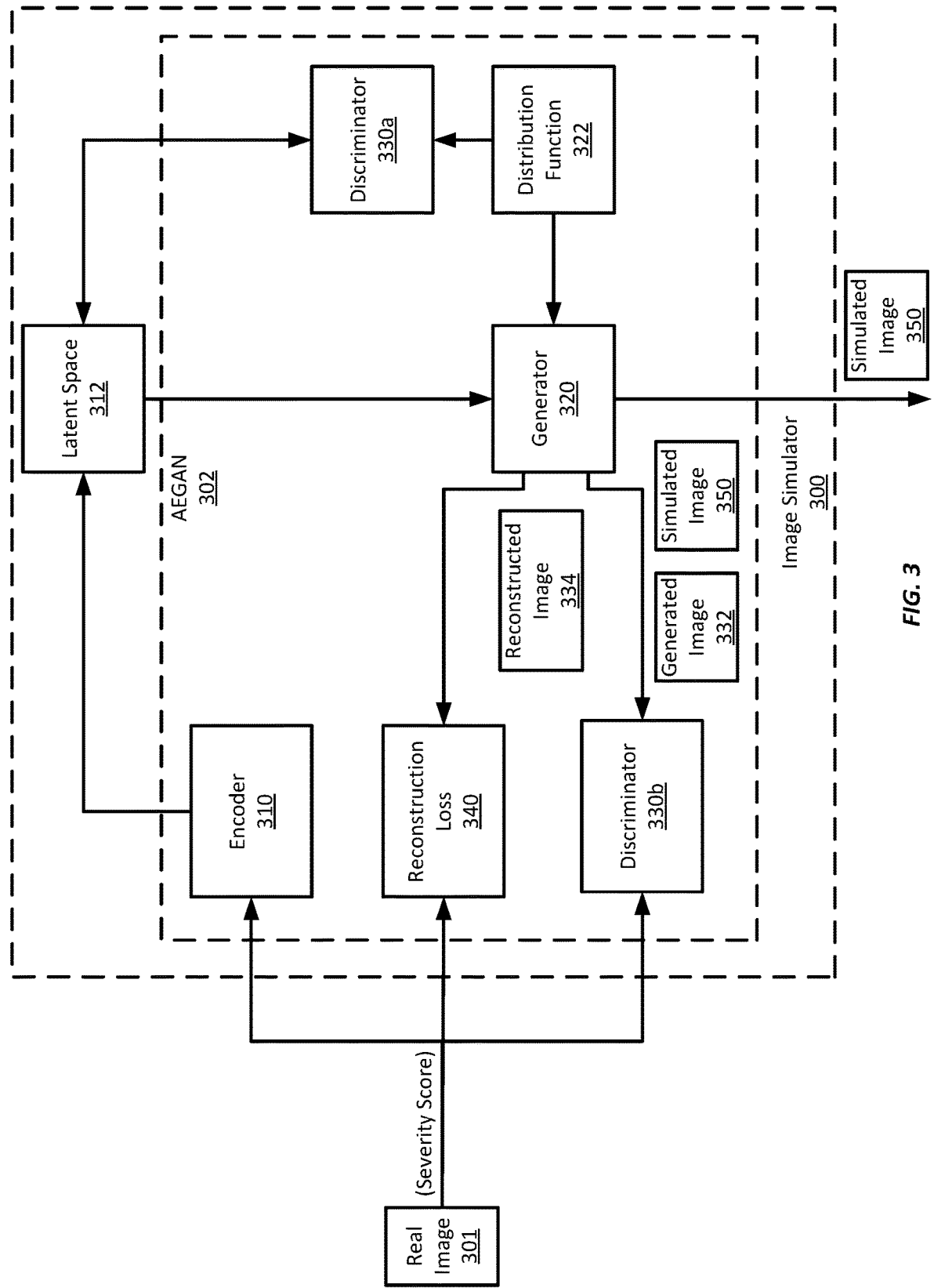
FIG. 3 shows an example system for simulating medical images using generative adversarial networks.

Referring now to FIG. 3, FIG. 3 illustrates an architecture for an image simulator 300 suitable for use with systems and methods for simulating medical images using GANs. In this example, the image simulator 300 employs an AEGAN 302 machine-learning architecture; however any suitable GAN may be employed, including a multi-scale GAN (e.g., a multi-scale AEGAN).

The AEGAN 302 includes an encoder 310, a generator 320 and two discriminators 330a-b. In addition, the AEGAN 302 makes use of a distribution function 322 and a reconstruction loss function (or just "loss function") 340. Generated image 332 and reconstructed image 334 are simulated images generated by the AEGAN 302 during training, but generally are not part of the AEGAN 302 architecture itself. Instead, they represent data generated and transmitted within the AEGAN 302. Latent space 312 is depicted as being external to the AEGAN 302 itself in this figure as it represents a data space rather than part of the processing components of the AEGAN 302; however, in some examples it may be considered as a part of the AEGAN 302. For example, in the case of an trained AEGAN, the latent space 312 may be considered as a part of the AEGAN 302 in some examples.

The encoder 310 receives real images 310, which it parameterizes and encodes within the latent space 312. The parameterized real image 301 is then used by the generator 320 to reconstruct the real image (reconstructed image 334), which is then used to compute a loss function 340 indicating the amount of data loss with respect to the original real image 301. The encoder 310 then adjusts parameters and associated weights based on the reconstruction loss calculated based on the reconstructed image 334 to try to reduce the value of the loss function 340. By iteratively reducing the loss function 340 over successive real images, the AEGAN 302 attempts to minimize the value for the loss function.

In addition to minimizing the loss function 340, data inserted into the latent space 312 is used by discriminator 330a to perform adversarial training between the latent space 312 and the distribution function 322. The distribution function 322 represents a desired distribution for data within the latent space 312. Any suitable distribution function may be employed, such as a normal (or Gaussian) distribution function.

To then train the AEGAN 302, a discriminator 330b takes a simulated or reconstructed image and evaluates it to determine if it is a "realistic" simulated image. Based on the result from the discriminator 330b, the image may be rejected if it is "unrealistic," or it may be accepted as "realistic." If the discriminator correctly identifies an image as unrealistic, the results are backpropagated to the generator to improve its model, and thus its image generation. Similarly, errors made by the discriminator 330b are backpropagated to it to improve its model and thus its ability to detect unrealistic generated images.

In some examples the AEGAN 302 maybe trained using both training images as well as additional information, such as a severity score for a corresponding affliction, or the identity of the affliction itself. Such information may be provided in a "label" along with the training image 301. Information from the label may be incorporated into the latent space or it may be provided to the generator or discriminator to help train the generator's or discriminator's models.

For example, real images with severity scores ranging from a minimum to maximum value, e.g., 1 to 10, may be represented as vectors (or tuples) within the latent space along with a corresponding label. A generator attempting to generate a realistic simulated image with a particular severity score may then generate a vector based on vectors in the latent space with a corresponding label, e.g., by interpolating between nearby vectors in the latent space. The simulated image along with the severity score, when provided to the discriminator, may be evaluated as being realistic or unrealistic as well as for its corresponding severity score. The discriminator then determines whether the simulated image is a "realistic" image for that severity score based on the latent space, an expected data distribution within the latent space, and a parameterization of the generated image. The results are used to further adjust the discriminator's model (if the discriminator incorrectly classifies the image), or the generator's model (if the discriminator accurately rejects the image as "unrealistic"). Thus, in addition to training the AEGAN 302 to generate realistic simulated images, it may be trained to generate such images based on inputted severity scores.

It should be appreciated that references above made to severity scores may be any suitable gradation applied to medical images. In some cases, e.g., with cancer, severity scores may correspond to stages of cancer development, while in some cases, severity scores may be based on widely recognized severity indicators or based on subjectively generated scores for the training images.

In addition, it should be appreciated that training images or seed images may be provided in a number of different resolutions. To handle such differences, the AEGAN 302 may indicate a resolution of an image as a part of a label in the latent space and insert the parameterized image into the latent space 312 using the resolution information.

After sufficient training images (whether real or simulated) have been provided to the AEGAN 302 such that the images it generates are sufficiently realistic, e.g., based on the output of the loss function 340 reaching an acceptable level or based on a review by a human evaluator, it may then be used to generate simulated images for use in a training or other live system.

Once the AEGAN 302 has been sufficiently trained, it may be used to generate simulated images for use. As discussed above, simulated images may be generated based on a desired severity of an affliction in the simulated image. Further, the trained AEGAN 302 may accept a seed image as an input and modify that image based on the latent space 312 and a corresponding severity score. For example, the AEGAN 302 may parameterize the seed image using the encoder 310, and then modify the parameters based on the latent space and the specified severity. The modified parameters may then be used by the generator 320 to generate a simulated image. Thus, a real pathology image 301 may be input into the image simulator 300, optionally with a severity score, and the image simulator 300, using the generator 320, generates and outputs a simulated image 350. Alternatively, a simulated image 350 may be generated without an inputted real image 301.

While the example above has been described in the context of an AEGAN, other techniques may be used as well. For example, any suitable type of GAN may be employed. Further, different types of autoencoders may be employed, such as variational autoencoders in a VAEGAN, etc.

Figure 4:
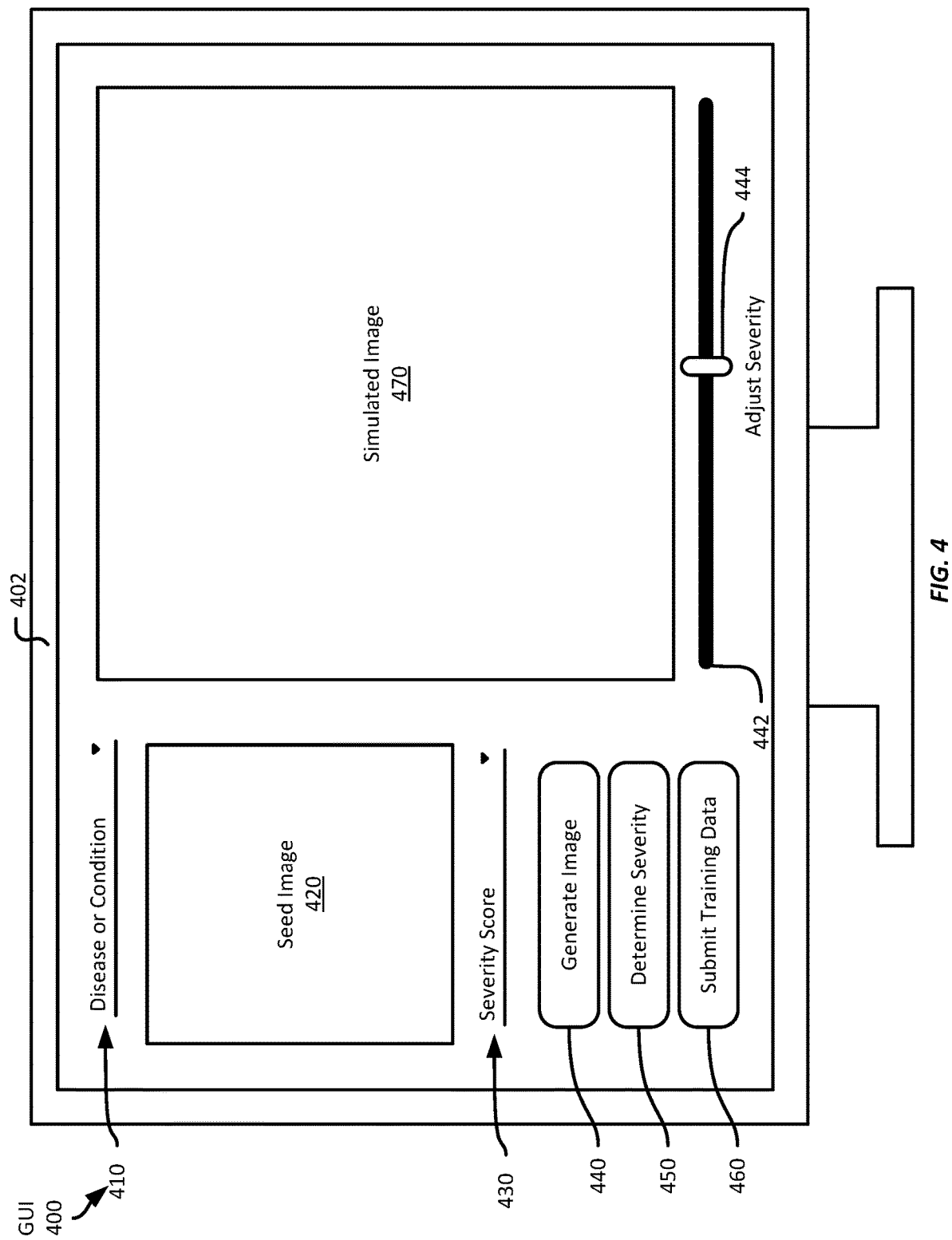
FIG. 4 shows an example graphical user interface of a system for simulating medical images using generative adversarial networks.

Referring now to FIG. 4, FIG. 4 shows an example user interface ("UI") for an image simulator, such as the image simulators 110, 300 shown in FIGS. 1 and 3. The UI shown in FIG. 4 is a graphical UI ("GUI") 400 displayed on a display screen 402. The GUI 400 and includes several GUI components to enable a user to interact with an image simulator, e.g., image simulators 110, 300. The GUI 400 provides options to allow a user to select an affliction of interest 410. Such a GUI component 410 may not be employed in some examples, such as in a case where only a single type of affliction is available for simulation.

The user may use GUI component 420 to select and view a seed image 420 and GUI component 430 to select a corresponding severity score to be provided to the image simulator 110, 300. As discussed above, one or both of a seed image 410 or a severity score is not required in some examples. Instead, the image simulator 110, 300 may be requested to generate a simulated realistic image of the selected affliction. If no severity score is provided, the GUI may select a severity score randomly or it may use a default score or the last inputted severity score.

After selecting a seed image 420 (optionally) and a severity score 430 (optionally), the user may select the "generate image" GUI component 440 to send a signal to the image simulator 110, 300 to cause it to generate a simulated image based on either (or both) the seed image 420 or the severity score 430 (or use a default or otherwise internally selected severity score, if the user does not provide one). The generated image is then received from the image simulator 110, 300 and displayed by GUI component 470. Alternatively, the user may provide a seed image without providing a severity score, and may then select GUI component 450 to obtain the severity score corresponding to the seed image. Finally, the user may select the "submit training data" GUI component 460 to submit the seed image and severity score to further train a GAN for simulating medical images.

In some examples, the user may be provided with one or more GUI components to allow the user to adjust the simulated image (or generate a new simulated image) by adjusting a severity score. In this example, the GUI 400 includes a slider bar 442 with a slide control 444 that may be moved to change a severity score. For example, if the slide control 444 is moved to the right, a severity score may be increased and supplied to the image simulator 110, 300, while movement to the left reduces the severity score. As the slide control 444 is moved, the resulting severity score may be sent to the image simulator, which may then generate a new simulated image and display it in GUI component 470. In some examples, the then-currently displayed image may be supplied as the seed image for the next simulated image. Thus, as the user slides the slide control 444, the GUI 400 may provide new simulated images 470 substantially in real time, thereby giving the illusion of an animation or movie of the pathology sample over time. Such functionality may allow a user to see and understand how affliction progression occurs in real time.

Figure 5A:
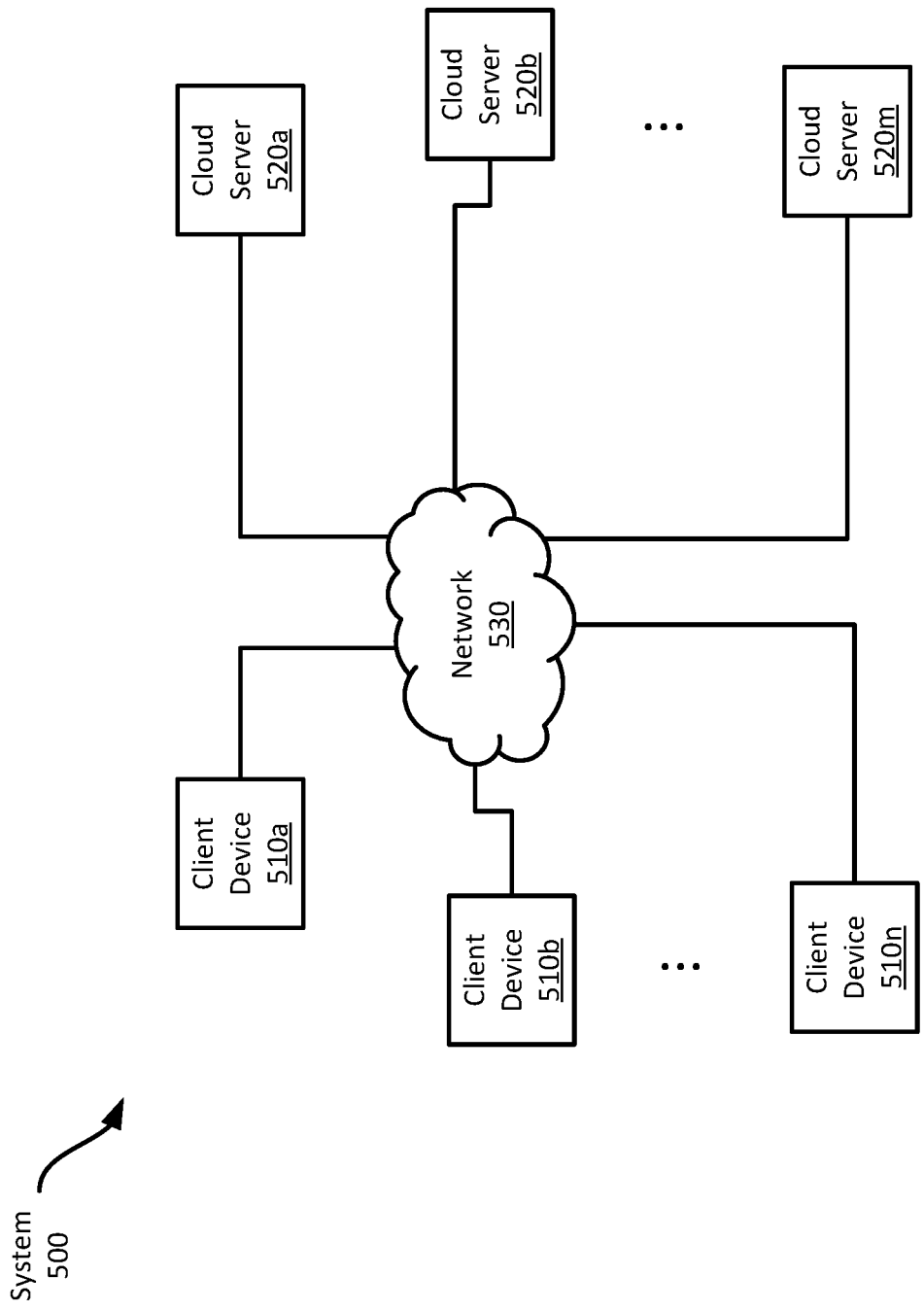
FIGS. 5A-5C show an example system for simulating medical images using generative adversarial networks.

Referring now to FIG. 5A, FIG. 5A shows an example system for simulating medical images using generative adversarial networks. In this example, the system 500 includes multiple client devices 510a-n and multiple cloud servers 520a-m, all interconnected by network 530. Note that 'n' and 'm' are used to denote any suitable number of client devices or cloud servers and that the number of client devices need not be the same as the number of cloud servers.

The client devices 510a-n may be used by users to execute software to simulate medical images using GANs, which may include training the GANs or using the GANs to generate simulated images.

To enable the clients 510a-c to perform such functionality, they may communicate with one or more cloud servers 520a-c. In this example, the clients 510a-c execute front-end software to present a GUI to the user, e.g., the GUI 400 shown in FIG. 4, to generate simulated images. The cloud servers 520a-c execute image simulation software, such as image simulation software 110, 300 described above with respect to FIGS. 1-3, which employ trained GANs to generate simulated images. Thus, a user may interact with a GUI, which transmits commands to the cloud servers 520a-c to cause the cloud servers 520 to train a GAN or to generate a simulated image using a GAN.

For example, a user at a client 510a may execute software at the client 510a, which connects to one of the cloud servers, e.g., cloud server 520a. The user may then select a type of affliction using the corresponding GUI element 410. They may then select a seed image 420 and a severity score 430, and may then activate the generate image GUI element 440. In response, the client 510a transmits the selected affliction, the seed image, and the severity score to the cloud server 520a, which uses a trained GAN, e.g., an AEGAN, corresponding to the selected affliction. The cloud server 520a then generates the requested simulated image and provides the image to the requesting client device 510a, which displays the simulated image using the corresponding GUI element 470.

Figure 5B:
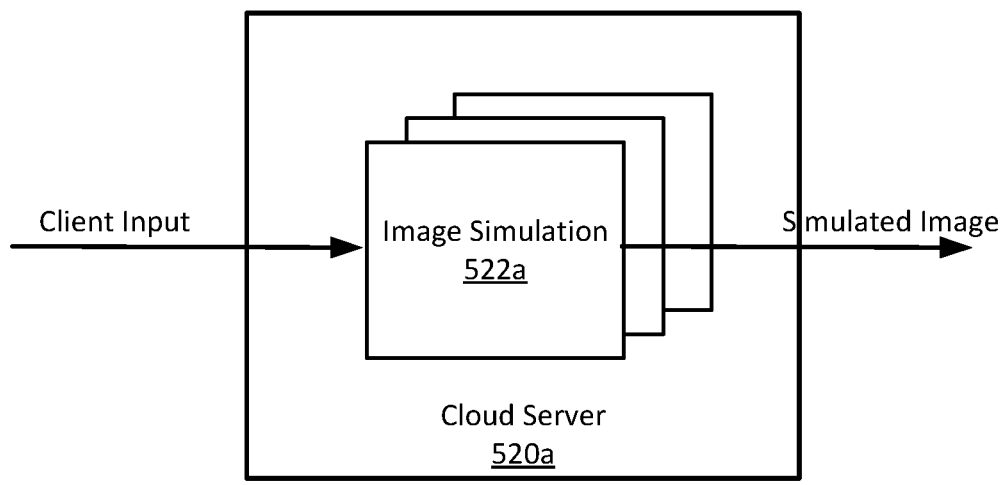

To enable such functionality, each of the cloud servers 520a-c may execute image simulation software trained based on one or more afflictions, which may enable the cloud servers 520a-c to generate simulated images for a variety of different afflictions. To enable such functionality, the cloud servers 520a-c may be configured in various ways. For example, referring to FIG. 5B, a cloud computer 520a may execute multiple different types of image simulation software 522a-n, each of which may be trained to generate simulated images of different afflictions. Thus, one image simulation software application 522a may be trained to generated simulated images of melanoma, while another image simulation software application 522b may be trained to generate simulated images of breast cancer. Thus, as client input is received by the cloud server 520a, the cloud server 520a first determines the type of simulated images to be generated and then executes the corresponding image simulation software application, e.g., application 522a. Subsequent client input related to the same affliction are routed to that particular image simulation software application 522a. Further, it should be appreciated that the cloud server 520a may receive client input from multiple different clients substantially simultaneously and, consequently, may execute various types of image simulation software 522a-j concurrently to generate any requested simulated images and provide them to the requesting client(s) 510a-c. As above with respect to 'm' and 'n,' 'j' denotes any arbitrary number of image simulation software applications 522a-j.

Figure 5C:
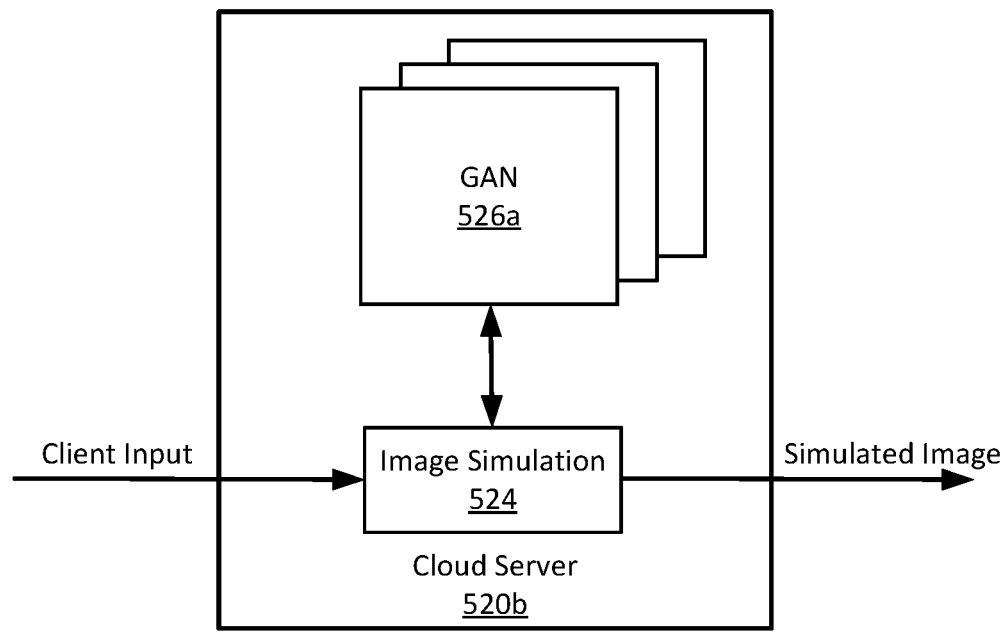

FIG. 5C illustrates a different configuration of a cloud server 520b. In this example, the cloud server 520b executes one image simulation software application 522b that uses one of multiple trained GANs 526a-k to generate simulated images. As client input is received from one or more client devices 510a-n, the input is provided to the image simulation software 524, which then selects the appropriate GAN 526a-k based on an affliction identified in the client input. The client input, e.g., a seed image or severity score, may be provided to the appropriate GAN 526*a-k*, which generates a simulated image based on the client input. The cloud server 520*b* then responds to the requesting client 510*a-n* with the generated image. As above with respect to 'm,' 'n,' and 'j,' 'k' denotes any arbitrary number of GANs 526*a-k*.

For the configurations of cloud servers 520*a* and 520*b* discussed above with respect to FIGS. 5B and 5C, it should be appreciated that in either case, the respective cloud server may execute as many instances of a particular image simulation application 522*a-j* or 524 based on client requests or cloud server capacity. Thus, for example, while cloud server 520*b* is shown with only one copy of image simulation software 524, which employs multiple different GANs 526*a-k* as described above, the cloud server 520*b* may in fact execute multiple instances of the image simulation software application 524 or multiple instances of a particular GAN 526*a-k* as needed to handle client input. Further, while the example cloud servers 520*a-b* are each illustrated as a single computing device, it should be appreciated that each may be implemented as a distributed group of computing devices functioning, from the clients' perspective, as a single cloud server.

While the discussions of the client devices 510*a-n* and cloud servers 520*a-m* has related to generating simulated images, they may also train GANs based on training images as described above with respect to FIGS. 1 and 3. In particular the client devices 510*a-n* may employ the GUI 400 to submit training data, e.g., an affliction, a seed image, and a severity score, by using the corresponding GUI element 460. The training data may be transmitted to the corresponding cloud server 520*a-m*, which uses the training data to further train a corresponding GAN, e.g., as a part of image simulation software 522*a-j* or one of GANs 526*a-k*.

Figure 6:
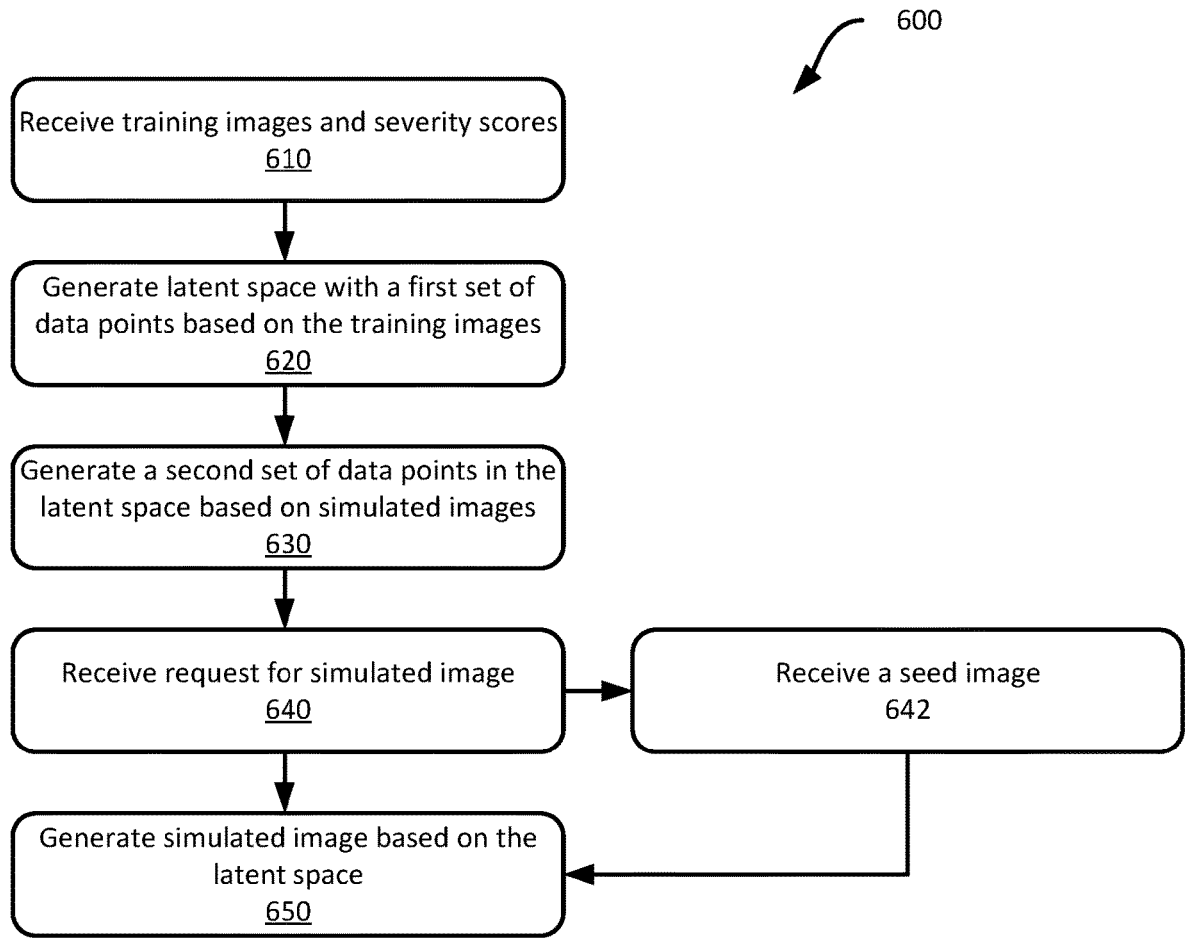
FIG. 6 shows an example method for simulating medical images using generative adversarial networks.

Referring now to FIG. 6, FIG. 6 shows an example method 600 for simulating medical images using GANs. The example method 600 will be discussed with respect to the image simulation software shown in FIG. 3 and the systems shown in FIGS. 1 and 5A-5C; however, any suitable image simulation software or system according to this disclosure may be employed.

At block 610, the image simulation software 300 receives one or more training medical images associated with an affliction and, for each training pathology image, a corresponding severity score. In this example, a computing device, e.g., the computing device 800 shown and described with respect to FIG. 8, access the training pathology image(s), which may be stored locally in memory on the computing device 800, e.g., in non-volatile storage, and provide the training image(s) to the image simulation software. In some examples, such as the example shown in FIG. 5A, a remote server, e.g., a cloud server 520*a-m*, may receive training images via a network 530 from one or more client devices 510*a-n*. The client devices 510*a-n* may transmit the training medical images using a GUI 400 as described in more detail with respect to FIG. 5A, or they may be provided using any other suitable technique, e.g., by uploading the medical images using the file transfer protocol ("FTP"), networked access to the cloud server's non-volatile storage device, etc.

In some examples, training medical images may include multiple images of the same piece of tissue, e.g., a multiple different resolutions, which may be referred to as a "stack" of images or a "multi-resolution stack." These multiple images may each be submitted as discrete images for purposes of training without reference to each other. However, in some examples, the images may be submitted and associated with each other. For example, a stack of five images may be submitted as five related files, or as a single image file with multiple embedded images of different resolutions.

Further, some examples may receive training images associated with multiple different afflictions and corresponding severity scores. In some such examples, the image simulation software may process each of the training images and a corresponding affliction identifier to insert the training images into the latent space. Because the different training images are associated with different afflictions, they each may be inserted into the same latent space, but labelled according to affliction, and thus will tend to cluster according to affliction.

At block 620, the image simulation software 300 generates a latent space having a first set of data points based on the received training medical images. For example, as discussed above with respect to FIG. 3, the training medical images may be parameterized into a set of data points by an autoencoder, e.g., encoder 310, as a part of an AEGAN 302 and inserted into the latent space 312, along with the corresponding severity score. The parameterized medical images may then be reconstructed and used to reduce or minimize an error value of a loss function 340 generally as discussed above with respect to FIG. 3. Using such a technique, an initial latent space 312 may be generated based on this first set of training medical images.

As discussed above with respect to block 610, in some examples, training medical images may include a multi-resolution stack of images. In some examples, these images may be processed separately, but associated within the latent space, e.g., using labels. Alternatively, the different resolution images may be treated as different portions or regions of a single image and encoded into the latent space together along with a label identifying the data as being a multi-resolution image. Such a label may include other information, such as identifications of which portions of the image are of which resolution, the number of different images represented, etc. Using such a technique, the image simulation software may embed multi-resolution and individual images within the same latent space.

At block 630, the image simulation software 300 generates a second set of data points in the latent space based on simulated medical images. As discussed above, to further densify the latent space, the AEGAN 302 may use adversarial training between a generator 320 and a discriminator 330*b* to generate additional data points within the latent space. To perform adversarial training, the generator 320 generates simulated medical images, which are provided to the discriminator 330*b*. The discriminator 330*b* attempts to determine whether the image is "realistic". If the discriminator 330*b* determines the simulated pathology image is "realistic," the discriminator 330*b* is updated to better identify simulated medical images. If the discriminator identifies the simulated pathology image as being a simulated pathology image, i.e., not realistic, the generator is updated to create more realistic medical images, based on the distribution function. As "realistic" medical images are generated, they are parameterized and used to populate the latent space 312. Over time, this adversarial training process can produce a dense latent space that can be used by a generator 320 to generate realistic simulated medical images of a particular affliction and having a desired severity.

While the description above with respect to block 630 is not specific to single images or multi-resolution stacks, multi-resolution stacks may be synthetically generated for adversarial training using these same techniques as described above. Thus, in some examples, image simulation software 300 may be capable of densifying a latent space that includes individual images or groups of associated images.

At block 640, the image simulation software 300 receives a request for a simulated image. In this example, the user uses the GUI 400 to identify an affliction and a severity score and selects the "generate image" GUI element 440. In some examples, the image simulation software 300 may be executed locally on the user's computing device; however, in some examples, as described above with respect to FIGS. 5A-5C, the image simulation software 300 may be executed by a cloud server 520*a-m* and, thus, the simulated image is generated at the cloud server 520*a-m* and may be later transmitted to a user's client device 510*a-n*, where it is displayed or otherwise stored. If a latent space includes data corresponding to multiple afflictions, the selected affliction may be used to obtain data from corresponding portions of the latent space. Alternatively, the identified affliction may be used to select a GAN or latent space corresponding to the identified affliction. Further, in some examples, the user may be presented with the option to request a multi-resolution stack of images, if the latent space includes data to enable generation of such stacks of images. If the user selects the option, such information may be received with the request for the simulated image.

In some examples, the user may use the GUI 400 to provide a seed image to the image simulation software 300. If the request for the simulated image at block 640 includes a seed image, the method proceeds to block 642. Otherwise, the method proceeds to block 650. It should be appreciated that the seed image may be a multi-resolution stack, in some examples.

To send a seed image at block 642, the user may use the GUI 400 to browse for the desired seed image and, once identified, may selected the "generate image" GUI element 440. The seed image is then provided to the image generation software 300, whether executing locally on the user's computing device or remotely, such as on a cloud server 520*a-m*. The seed image may be received along with the request for the simulated image or separately from the request itself, such as in a subsequent message or file transfer transaction.

At block 650, the image simulation software 300 uses the AEGAN 302 to generate a simulated pathology image or multi-resolution stack of images for the affliction based on the severity score. Thus, in this example, the AEGAN 302 generates a set of image parameters based on the latent space and then generates an image using those image parameters, similar to how the generator reconstructs a training image to minimize the loss function. If the AEGAN 302 received a seed image with the request, the AEGAN 302 parameterizes the seed image using the encoder 310. The parameters may then be adjusted by the generator 320 based on a specified severity level and the data within the latent space 312. The adjusted parameters may then be used by the generator 320 to generate a simulated pathology image in the same way a reconstructed image was created from a real image during a training phase, as described above with respect to FIG. 3.

After it is generated, the simulated pathology image is provided to the GUI 400, which displays it in the simulated image GUI element 470. In examples where the image simulation software 300 is executed locally on the user's computing device, the image simulation software simply displays the generated pathology image for the user. In other examples where the image simulation software 300 is executed remotely from the user's computing device, such as in the case of the system 500 of FIG. 5A, the generated pathology image is transmitted to the user's computing device, e.g., via a network 530, where it is received and displayed. Once the simulated pathology image has been displayed, the user may save the image for later use, zoom or pan within the image, or otherwise interact with the image.

After completing the method 600, it may be performed again, such as based on a new request from the user, or based on changes made in the GUI, e.g., to the slider control 444 to adjust the severity of the affliction in the generated image.

Figure 7:
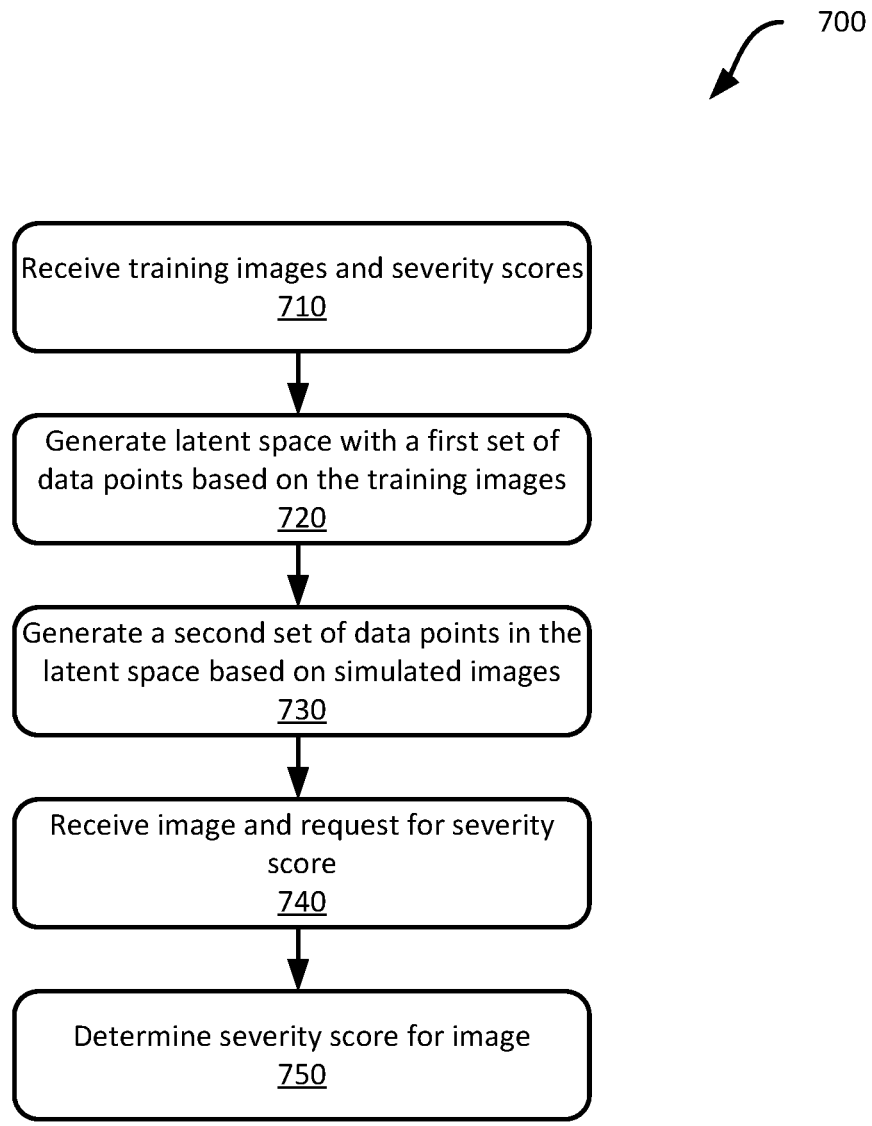
FIG. 7 shows an example method for determining a severity score for an image of an affliction using generative adversarial networks.

Referring now to FIG. 7, FIG. 7 shows an example method for simulating medical images using GANs. The example method 600 will be discussed with respect to the image simulation software shown in FIG. 3 and the systems shown in FIGS. 1 and 5A-5C; however, any suitable image simulation software or system according to this disclosure may be employed.

At block 710, the image simulation software 300 receives one or more training medical images associated with an affliction and, for each training pathology image, a corresponding severity score generally as discussed above with respect to block 610.

At block 720, the image simulation software 300 generates a latent space having a first set of data points based on the received training medical images generally as discussed above with respect to block 620.

At block 730, the image simulation software 300 generates a second set of data points in the latent space based on simulated medical images generally as discussed above with respect to block 630.

At block 740, the image simulation software 300 receives a seed image and a request for a severity score. In this example, the user uses the GUI 400 to identify an affliction and provide a seed image. The user may then select a GUI component 450 to obtain a severity score corresponding to the seed image.

To send a seed image, the user may use the GUI 400 to browse for the desired seed image and, once identified, may selected the "determine severity" GUI element 440. The seed image is then provided to the image generation software 300, whether executing locally on the user's computing device or remotely, such as on a cloud server 520*a-m*. The seed image may be received along with the request for the severity score or separately from the request itself, such as in a subsequent message or file transfer transaction.

At block 750, the image simulation software 300 uses the AEGAN 302 to parameterize the seed image and determine a corresponding location within the latent space 312. Based on the determined location, the image simulation software 300 can determine a severity score based on the parameterized image's proximity to other data in the latent space and the corresponding severity scores.

After determining a severity score for the seed image, it may be provided to the user via the GUI, such as by updating the severity score GUI component 430 to show the determined severity score.

As discussed above with respect to FIG. 6, in some examples, the image simulation software 300 may be executed locally on the user's computing device; however, in some examples, as described above with respect to FIGS. 5A-5C, the image simulation software 300 may be executed by a cloud server 520*a-m* and, thus, the seed image and the request for the severity score may be transmitted to the cloud server 520*a-m* from a user's client device 510*a-n*, and the determined severity score may be transmitted to the user's client device where it may be displayed.

Figure 8:
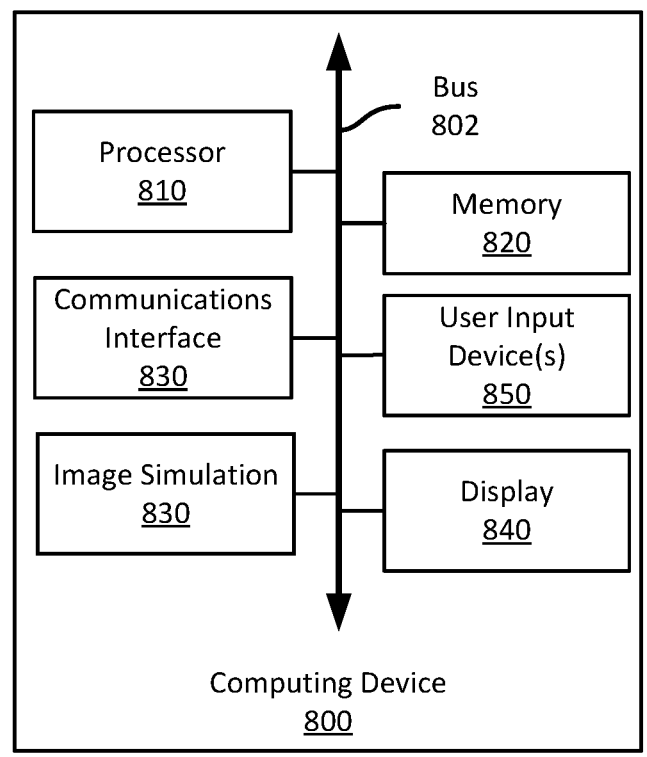
FIG. 8 shows an example computing device suitable for simulating medical images using generative adversarial networks according to various examples.

Referring now to FIG. 8, FIG. 8 shows an example computing device 800 suitable for use in example systems or methods for simulating medical images using GANs according to this disclosure. The example computing device 800 includes a processor 810 which is in communication with the memory 820 and other components of the computing device 800 using one or more communications buses 802. The processor 810 is configured to execute processor-executable instructions stored in the memory 820 to perform one or more methods for simulating medical images using GANs according to different examples, such as part or all of the example method 600 described above with respect to FIG. 6. The computing device, in this example, also includes one or more user input devices 850, such as a keyboard, mouse, touchscreen, microphone, etc., to accept user input. The computing device 800 also includes a display 840 to provide visual output to a user.

The computing device 800 also includes a communications interface 840. In some examples, the communications interface 830 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically-configured hardware, such as field-programmable gate array (FPGA) specifically to execute the various methods according to this disclosure. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example one or more non-transitory computer-readable media, that may store processor-executable instructions that, when executed by the processor, can cause the processor to perform methods according to this disclosure as carried out, or assisted, by a processor. Examples of non-transitory computer-readable medium may include, but are not limited to, an electronic, optical, magnetic, or other storage device capable of providing a processor, such as the processor in a web server, with processor-executable instructions. Other examples of non-transitory computer-readable media include, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code to carry out methods (or parts of methods) according to this disclosure.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; Band C only; and A and Band C.

The invention claimed is:

1. A method comprising:
receiving, by a trained generative adversarial network ("GAN"), a severity score associated with an affliction, the severity score identifying a stage of progression for the affliction; and
generating and outputting, using the trained GAN, a simulated pathology image based on a latent space and the severity score, the latent space comprising:
a first set of data points indicating parameters associated with a set of training pathology images associated with the affliction and depicting different stages of progression for the affliction, and
a second set of data points generated by the GAN based on the first set of data points, the parameters comprising indications of severity level of the affliction.

2. The method of claim 1, further comprising receiving a seed pathology image associated the severity score and a corresponding affliction, and wherein generating and outputting the simulated pathology image comprises modifying the seed pathology image.

3. The method of claim 1, wherein:
the set of training pathology images is associated with a plurality of afflictions and depict different stages of progression for each of the afflictions; and
the parameters comprising indications of a severity level of the respective affliction.

4. The method of claim 1, wherein the GAN comprises an autoencoder generative adversarial neural network ("AE-GAN").

5. The method of claim 1, wherein the set of training pathology images comprises multi-resolution pathology image stacks.

6. The method of claim 1, wherein the GAN comprises a variational autoencoder.

7. The method of claim 1, wherein receiving the severity score comprises receiving the severity score from a remote computing device.

8. A method comprising:
receiving, by a trained generative adversarial network ("GAN"), a seed pathology image associated with an affliction; and
generating and outputting, using the trained GAN, a severity score based on a latent space and the seed pathology image, the severity score identifying a stage of progression for the affliction, the latent space comprising:
a first set of data points indicating parameters associated with a set of training pathology images associated with the affliction and depicting different stages of progression for the affliction, and
a second set of data points generated by the GAN based on the first set of data points, the parameters comprising indications of a severity level of the affliction.

9. The method of claim 8, wherein the GAN comprises an autoencoder generative adversarial neural network ("AE-GAN").

10. The method of claim 8, wherein the set of training pathology images comprises multi-resolution pathology image stacks.

11. The method of claim 8, wherein the GAN comprises a variational autoencoder.

12. The method of claim 8, wherein receiving the seed pathology image comprises receiving the seed pathology image from a remote computing device.

13. A system comprising:
a non-transitory computer-readable medium; and
one or more processors in communication with the non-transitory computer-readable medium, the one or more processors configured to execute processor-executable instructions stored in the non-transitory computer-readable medium to:
receive, by a trained generative adversarial network ("GAN"), a severity score associated with an affliction, the severity score identifying a stage of progression for the affliction; and
generate and output, using the GAN, a simulated pathology image based on a latent space and the severity score, the latent space comprising:
a first set of data points indicating parameters associated with a set of training pathology images associated with the affliction and depicting different stages of progression for the affliction, and
a second set of data points generated by the GAN based on the first set of data points, the parameters comprising indications of severity level of the affliction.

14. The system of claim 13, wherein the one or more processors are configured to execute further processor-executable instructions stored in the non-transitory computer-readable medium to receive a seed pathology image associated the severity score and a corresponding affliction, and modify the seed pathology image.

15. The system of claim 13, wherein:
the set of training pathology images is associated with a plurality of afflictions and depict different stages of progression for each of the afflictions; and
the parameters comprising indications of a severity level of the respective affliction.

16. The system of claim 13, wherein the GAN comprises an autoencoder generative adversarial neural network ("AE-GAN").

17. The system of claim 13, wherein the set of training pathology images comprises multi-resolution pathology image stacks.

18. The system of claim 13, wherein the GAN comprises a variational autoencoder.

19. The system of claim 13, processor-executable instructions stored in the non-transitory computer-readable medium to receive the severity score from a remote computing device.

20. A non-transitory computer-readable medium comprising processor-executable instructions configured to cause one or more processors to:
receive, by a trained generative adversarial network ("GAN"), a severity score associated with an affliction, the severity score identifying a stage of progression for the affliction; and
generate and output, using the GAN, a simulated pathology image based on a latent space and the severity score, the latent space comprising:
a first set of data points indicating parameters associated with a set of training pathology images associated with the affliction and depicting different stages of progression for the affliction, and
a second set of data points generated by the GAN based on the first set of data points, the parameters comprising indications of severity level of the affliction.

21. The non-transitory computer-readable medium of claim 20, further comprising processor-executable instructions configured to cause the one or more processors to receive a seed pathology image associated the severity score and a corresponding affliction, and modify the seed pathology image.

22. The non-transitory computer-readable medium of claim 20, wherein:
the set of training pathology images is associated with a plurality of afflictions and depict different stages of progression for each of the afflictions; and
the parameters comprising indications of a severity level of the respective affliction.

23. The non-transitory computer-readable medium of claim 20, wherein the GAN comprises an autoencoder generative adversarial neural network ("AEGAN").

24. The non-transitory computer-readable medium of claim 20, wherein the set of training pathology images comprises multi-resolution pathology image stacks.

25. The non-transitory computer-readable medium of claim 20, wherein the GAN comprises a variational autoencoder.

26. The non-transitory computer-readable medium of claim 20, further comprising processor-executable instructions configured to cause the one or more processors to receive the severity score from a remote computing device.

27. The method of claim 1, wherein receiving the severity score is based on a position of a slider in a graphical user interface, and further comprising:
receiving a new severity score based on a changed position of the slider; and
generating and outputting, using the GAN, a second simulated pathology image based on the latent space and the new severity score.

* * * * *